(12) United States Patent
Digioia

(10) Patent No.: US 11,028,036 B2
(45) Date of Patent: Jun. 8, 2021

(54) PROCESS FOR THE HYDROLYSIS OF DICARBOXYLIC ACID TRIGLYCERIDES

(71) Applicant: NOVAMONT S.P.A., Novara (IT)

(72) Inventor: Francesca Digioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 113 days.

(21) Appl. No.: 16/306,154

(22) PCT Filed: Jun. 5, 2017

(86) PCT No.: PCT/EP2017/063615
§ 371 (c)(1),
(2) Date: Nov. 30, 2018

(87) PCT Pub. No.: WO2017/211764
PCT Pub. Date: Dec. 14, 2017

(65) Prior Publication Data
US 2020/0325094 A1    Oct. 15, 2020

(51) Int. Cl.
*C07C 51/09* (2006.01)
*C07C 55/02* (2006.01)
*C07C 55/18* (2006.01)

(52) U.S. Cl.
CPC .............. *C07C 51/09* (2013.01); *C07C 55/02* (2013.01); *C07C 55/18* (2013.01)

(58) Field of Classification Search
CPC ......... C07C 51/09; C07C 51/16; C07C 51/21; C07C 51/25; C07C 55/02; C07C 55/18; C07C 55/21; C11C 1/04
See application file for complete search history.

(56) References Cited

U.S. PATENT DOCUMENTS 8,835,662 B2 *   9/2014   Bieser ................. C07C 51/245
                                                         554/132

FOREIGN PATENT DOCUMENTS

| GB | 594-141 A | 11/1947 |
| JP | 2007-009017 A | 1/2007 |
| WO | WO-2011/080296 A1 | 7/2011 |

* cited by examiner

*Primary Examiner* — Yate' K Cutliff
(74) *Attorney, Agent, or Firm* — Polsinelli PC

(57) ABSTRACT

This invention relates to an improved hydrolysis process for the preparation of dicarboxylic acids in which an organic phase comprising triglycerides of carboxylic acids having more than one acid functional group and a mixture comprising dicarboxylic acids, glycerine and partial esters of glycerine are mixed with water and hydrolysed at temperatures of between 50 and 350° C., and at pressures of or above the equilibrium vapor pressure. This process makes it possible to obtain high hydrolysis yields, even in short times.

20 Claims, 1 Drawing Sheet

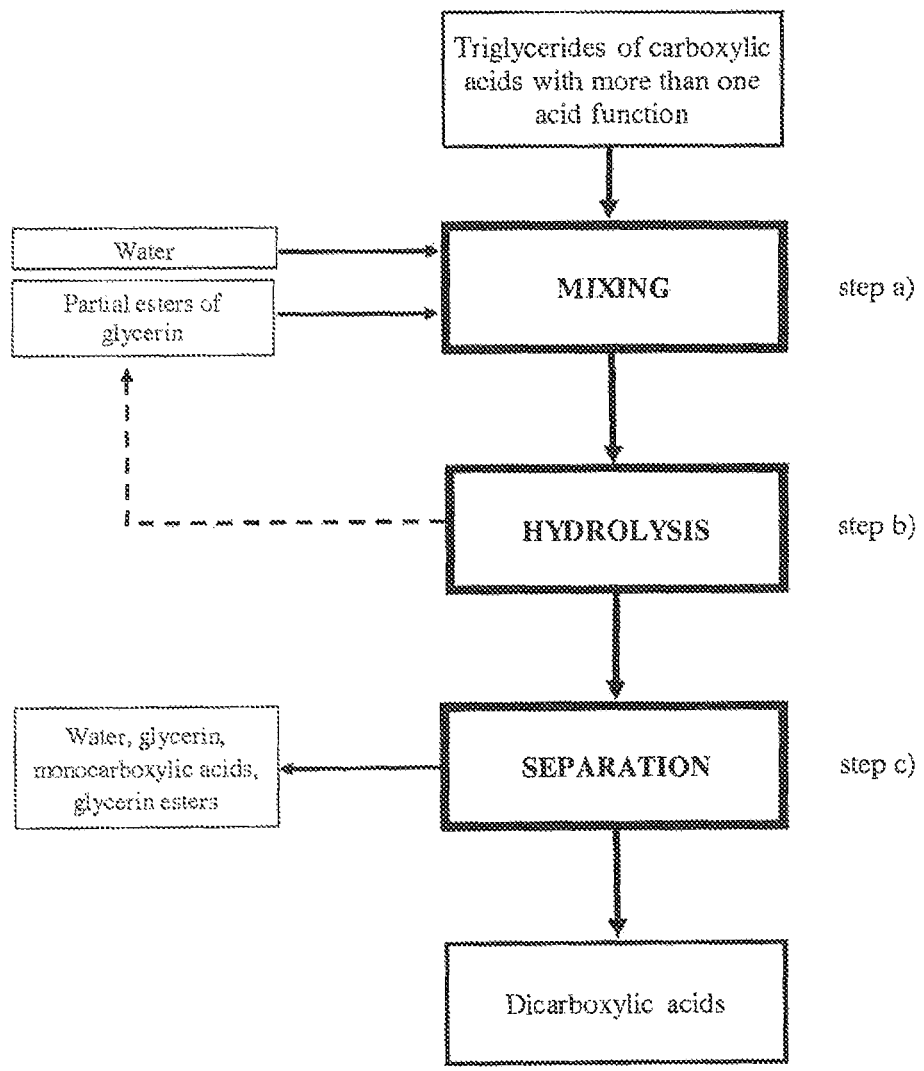

PROCESS FOR THE HYDROLYSIS OF DICARBOXYLIC ACID TRIGLYCERIDES

CROSS REFERENCE TO RELATED APPLICATIONS

This application is the National Phase of Application No. PCT/EP2017/063615 filed Jun. 5, 2017, which claims priority to Application No. 102016000057689 filed in Italy on Jun. 6, 2016 under 35 U.S.C. § 119. The entire contents of each application are hereby incorporated by reference.

DESCRIPTION

This invention relates to an improved process for the hydrolysis of carboxylic acid triglycerides having more than one acid functional group, carried out using water under sub-critical conditions and in the presence of mono- and di-esters of glycerine with dicarboxylic acids, for the preparation of dicarboxylic acids.

BACKGROUND OF DISCLOSURE

Technical Field

Vegetable oils are now an important raw material for the chemical industry because of the ever-increasing need to identify raw materials of renewable origin as an alternative to conventional petroleum sources.

Starting from vegetable oils containing monounsaturated fatty acid triglycerides, and through oxidative cleavage process such as those described in patent applications WO 2008/138892 and WO 2011/080296 it is possible to obtain carboxylic acid triglycerides with more than one acid functional group, which are in turn converted through hydrolysis reactions to important intermediates for the preparation of polyesters, such as, for example, the saturated dicarboxylic acids azelaic acid or brassylic acid.

It has therefore become useful to develop new industrial processes and to improve the performance of known processes for the production of dicarboxylic acids and, in particular, hydrolysis reactions.

The hydrolysis reactions of triglycerides present in vegetable oils and fats are typically catalysed by bases (i.e. saponification reactions) or acids, that can be carried out through a route using enzymes, for example, by means of lipases, or at high pressures and temperatures, such as, for example, in application WO 2008/138892, in which the hydrolysis reaction is carried out at a temperature of 180° C. and requires times of approximately 3 hours, or using super-critical $CO_2$.

One possible alternative industrial embodiment comprises the reaction with water alone under critical conditions (374° C. and approximately 220 bar) or near-critical conditions. Making use of the ability of water to dissolve apolar compounds and obtain homogeneous systems, under such conditions it is in fact possible to avoid the use of organic solvents, at least partly reducing the environmental impact of the process.

A process operating under similar conditions is described in patent application WO 97/07187, in which the fundamental role of the addition of water and the removal of glycerine formed during the course of the reaction in order to be able to reach completion is clearly indicated. However, residence at high temperatures may give rise to triglyceride degradation phenomena, such as, for example, pyrolysis, decomposition or polymerisation. On the basis of the known art, in batch systems the optimum operating temperatures for the hydrolysis of vegetable oils under sub-critical conditions are in fact around 270-280° C. (see Ind. Eng. Chem. Res. 1997, 36, 932-935). Conversely, when operating in continuous systems, such as for example tubular reactors, minimum conversions (around 22%) are obtained at 270° C., while temperatures of around 330-340° C. are needed in order to obtain good conversions. High conversions can nevertheless be achieved in both the abovementioned cases through the use of high water:oil ratios of between 2.5:1 and 5:1, if not higher (Green Chemistry, 1999, 1, 261-264). Use of such large quantities of water nevertheless constitutes a disadvantage from the point of view of industrial production.

Application WO 2011/080296 describes the preparation of dicarboxylic acids through a hydrolysis reaction of carboxylic acid triglycerides having more than one acid functional group with water under sub-critical conditions, carried out at 300° C. and 105 bar in a tubular reactor with piston flow (Plug Flow Reactor). Under such conditions, in the presence of a water:oil ratio of approximately 2:1 by weight, a sufficient hydrolysis yield is achieved in short times, limiting the formation of degradation products.

BRIEF SUMMARY OF THE DISCLOSURE

It has now surprisingly been discovered that by also feeding a specific quantity of partial esters of glycerine with dicarboxylic acids to the hydrolysis reactor in addition to the triglycerides of carboxylic acids having more than one acid functional group it is possible to perform a hydrolysis reaction with water at high temperature and without the need for catalyst, obtaining a further improvement in reaction yields for the same operating conditions, and as a consequence, also in the final yield of dicarboxylic acids. The said partial esters of glycerine are also efficient when fed in the form of a mixture further comprising dicarboxylic acids and/or glycerine. In addition to this, by carrying out the hydrolysis reaction of the said triglycerides in the presence of the said partial esters of glycerine with dicarboxylic acids, it is possible to achieve a high reaction yield under conditions which are even milder than those described above.

The object of this invention is therefore a process for the preparation of dicarboxylic acids from triglycerides of carboxylic acids having more than one acid functional group comprising the steps of:
a) mixing water with an organic phase consisting of triglycerides of carboxylic acids having more than one acid function and from 3 to 20% by weight, preferably from 5 to 10% by weight (with respect to the weight of the organic phase), of a mixture comprising partial esters of glycerine with at least a dicarboxylic acid;
b) hydrolysing the mixture obtained at the end of step a) in one or more hydrolysis reactors at temperatures of between 150 and 350° C., and at pressures corresponding to or higher than the equilibrium vapor pressure, preferably at temperatures between 240 and 320° C. and pressures of between 40 and 110 bar, more preferably at temperatures of between 260 and 310° C. and pressures of between 67 and 110 bar, and even more preferably at temperatures of between 270 and 305° C. and pressures of between 75 and 100 bar;
c) separating out the dicarboxylic acids from the hydrolysis product obtained in step b).

The said organic phase of step a) preferably comprises from 0.01 to 15% by weight, more preferably from 0.05 to 7% by weight, of the said partial esters of glycerine with respect to the weight of the organic phase.

The said mixture comprising partial esters of glycerine of step a) can advantageously be obtained from the hydrolysis product obtained in step b), before or after the dicarboxylic acids are separated out in step c) of the process.

According to a preferred aspect of the invention, the said mixture comprising partial esters of glycerine of step a) further comprises dicarboxylic acids and/or glycerine.

The process according to the invention will be described in greater detail below.

BRIEF DESCRIPTION OF THE DRAWING

The Figure is a flow diagram of a process according to the present disclosure.

DETAILED DESCRIPTION OF THE DISCLOSURE

FIG. 1 shows a flow diagram of one aspect of the process in which the water and the triglycerides of carboxylic acids having more than one acid functional group are mixed in step a) with partial esters of glycerine partly deriving from the product of the hydrolysis reactor. Each step in the process according to the invention can be carried out in batch, continuous or semi-continuous mode, in one or more reactors placed in series or in parallel.

Any container capable of mixing the organic phase with an aqueous phase, such as, for example, a static or dynamic mixer, can be used as the reactor for step a).

The reactor for step b) is the same as or different from a reactor for step a) and is preferably of the tubular type with piston flow (Plug Flow Reactor).

According to a particularly preferred aspect of the invention, the process is performed by continuously feeding to the hydrolysis reactor or reactors of step b) at least a part of the hydrolysis product that is obtained at the end of step b), before or after the separation of step c).

The material undergoing hydrolysis in this process (organic phase) contains one or more triglycerides of carboxylic acids having more than one acid functional group, which are the same or different from each other and contain at least one acyl group of a dicarboxylic acid.

By "dicarboxylic acids" in this application are meant aliphatic diacids, preferably of the alpha-omega type, selected for example from oxalic acid, malonic acid, succinic acid, glutaric acid, adipic acid, pimelic acid, suberic acid, azelaic acid, sebacic acid, undecanedicarboxylic acid, dodecanedicarboxylic acid, brassylic acid, tetradecanedicarboxylic acid and pentadecanedicarboxylic acid.

According to a preferred aspect of the invention the triglycerides of carboxylic acids having more than one acid functional group used as the starting material advantageously contain $C_6$-$C_{24}$ chain dicarboxylic acids, preferably belonging to the group comprising suberic acid, azelaic acid, sebacic acid, undecanedicarboxylic acid, dodecandicarboxylic acids, brassylic acid and mixtures thereof. Preferably the said triglycerides mainly contain azelaic acid.

In addition to the aforesaid acyclic groups of dicarboxylic acids, the said triglycerides typically also contain one or more acyl groups of monocarboxylic acids which are the same or different from each other. The said monocarboxylic acids are aliphatic monoacids and may be saturated or unsaturated, substituted or unsubstituted; they will have a chain length of $C_6$-$C_{24}$, more commonly $C_9$-$C_{24}$. Examples of unsubstituted monocarboxylic acids are palmitic, stearic, oleic, arachidic, behenic and lignoceric acids.

Examples of substituted monocarboxylic acids are long-chain monocarboxylic acids having one or more ketone groups or hydroxyl groups in non-terminal positions, such as $C_{12}$-$C_{24}$ carboxylic acids containing at least one ketone group or $C_{12}$-$C_{24}$ hydroxy acids containing at least one secondary hydroxyl group. Specific examples of substituted monocarboxylic acids which may be present are 9-hydroxystearic acid, 9-ketostearic acid, 10-ketostearic acid and 10-hydroxystearic acid.

The said substituted monocarboxylic acids may contain two adjacent hydroxyl groups, such as dihydroxypalmitic, dihydroxystearic, dihydroxyoleic, dihydroxyarachidic and dihydroxy-behenic acids, or a hydroxyl group adjacent to a ketone group.

The triglycerides of carboxylic acids with more than one acid functional group undergoing this process may optionally be in the form of a mixture with one or more monocarboxylic and/or dicarboxylic acids. Examples of monocarboxylic acids which may occur free in a mixture are saturated or unsaturated aliphatic monoacids having a chain of between $C_2$ and $C_{24}$, which may be linear or branched, substituted or unsubstituted. Examples of dicarboxylic acids which may occur free in a mixture correspond to those listed above with possible acyl substituents in the triglycerides.

Triglycerides of carboxylic acids with more than one acid functional group undergoing the process may be advantageously obtained for example from unsaturated triglycerides present in vegetable oils or animal fats, using known techniques. Oxidative cleavage reactions of the double bonds present in the acyl groups of the said unsaturated triglycerides are one example.

These reactions may be carried out using one or more oxidising agents such as, for example, inorganic and organic peroxides, peracids, nitric acid, permanganates, periodates, $O_2$, $O_3$ or mixtures of gases containing them.

In particular the mixtures of triglycerides obtained by processes of the oxidative cleavage of unsaturated triglycerides in which peroxides such as hydrogen peroxide $O_2$ or mixtures containing $O_2$ are used are advantageously used as a starting material for this process. Preferred examples are the processes described in applications WO 2008/138892, WO 2011/080296 or WO 2013/079849 A1.

Particularly preferred are mixtures of triglycerides containing dicarboxylic acids obtained after step c) of separating out the saturated monocarboxylic acids by means of the processes described in applications WO 2008/138892 and WO 2011/080296, incorporated here as a reference.

This invention therefore also relates to a process for the hydrolysis of triglycerides of carboxylic acids having more than one acid functional group carried out starting from vegetable oils comprising triglycerides of unsaturated acids and comprising, prior to the hydrolysis reaction, the steps of:

1) reacting the said triglycerides of unsaturated carboxylic acids with an oxidising agent and a catalyst activating the oxidisation reaction of the olefin double bond in order to obtain an intermediate compound containing vicinal diols, and
2) causing the said intermediate compound containing vicinal diols, an oxidising agent containing molecular oxygen and a catalyst activating the oxidation reaction of vicinal diols to carboxylic groups to react, obtaining monocarboxylic acids and triglycerides of carboxylic acids with more than one acid functional group;
3) separating, preferably by distillation, a fraction of the said monocarboxylic acids obtaining a mixture comprising the said triglycerides of carboxylic acids with more than one acid functional group.

Unsaturated carboxylic acid triglycerides suitable for use in abovementioned step 1) contain monounsaturated and/or polyunsaturated carboxylic acids, such as for example, 9-tetradecenoic (myristoleic) acid, 9-hexadecenoic (palmitoleic) acid, 9-octadecenoic (oleic) acid, 12-hydroxy-9-octadecenoic (ricinoleic) acid, 9-eicosenoic (gadoleic) acid, 13-docosenoic (erucic) acid, 15-tetracosenoic (nervonic) acid, 9,12-octadecadienoic (linoleic) acid, and 9,12,15-octadecatrienoic (linolenic) acid. Preferred are triglycerides containing monounsaturated carboxylic acids; the use of oleic acid triglycerides from the oxidative cleavage of which mainly triglycerides of azelaic acid are obtained is particularly advantageous according to this aspect of the process.

The said triglycerides of unsaturated carboxylic acids are preferably present in vegetable oils or mixtures thereof, which therefore constitute the preferred raw material fed to the process according to this aspect of the invention. By vegetable oils are meant both the unmodified product of pressing, or an oil which has undergone chemical or chemical-physical modifications, such as for example, purification, hydrogenation or enzyme enrichment treatments. Examples of preferred vegetable oils are soya oil, olive oil, castor oil, sunflower oil, peanut oil, maize oil, palm oil, jatropha oil, cuphea oil, oils from Brassicaceae, such as *Crambe abyssinica, Brassica carinata, Brassica napus* (colza),), Carduae oils such as *Cynara cardunculus* (thistle), *Silybum marianum, Carthamus tinctorius*, Lesquerella, and other oils having a high monounsaturated acids content. The use of sunflower oil and thistle oils is particularly preferred.

The oxidising agent used to carry out step 1) (hydroxylation) is selected from osmium tetroxide, permanganates, hydrogen peroxide, alkyl-hydroperoxides and percarboxylic acids, such as for example performic acid, peracetic acid or perbenzoic acid. The said oxidising agent is more preferably an aqueous solution of hydrogen peroxide in concentrations of between 30 and 80% by weight, preferably between 40 and 70% and even more preferably between 49 and 65%.

The diol resulting from hydroxylation step 1) is caused to react—during oxidative cleavage step 2)—with oxygen or a compound containing oxygen. The use of air is particularly advantageous. Air enriched with oxygen may also be used.

The catalyst for step 1 belongs to the group of transition elements. Fe, Mn, Mo, Nb, Os, Re, Ti, V, W, Zr and their acids, alkali metal salts and complexes are advantageously used as homogeneous or heterogeneous phase catalysts, possibly in supported or nanostructured form. The use of tungstic acid and/or its derivatives, such as phosphotungstic acid, is particularly preferred. The said catalyst is present in quantities of between 0.03% and 3% in moles, preferably between 0.05% and 1.8% in moles, and even more preferably between 0.06% and 1.5% in moles with respect to the total moles of unsaturations.

As far as the catalyst for step 2) of oxidative cleavage is concerned, this belongs to the group of transition elements. Ce, Cr, Co, Cu, Mn, Mo, Re, Os, V and W and their acids, alkali metal salts and complexes are advantageously used as homogeneous phase catalysts. The use of cobalt suits such as, for example, acetate, chloride, sulfate, bromide and nitrate, used in quantities between 0.05% and 3% in moles, preferably between 0.1% and 2% in moles and even more preferably between 0.3% and 1.5% in moles with respect to the diol produced in step 1) is particularly preferred. Particularly preferred is the use of cobalt acetate and cobalt chloride.

An inorganic acid, for example, phosphoric acid, sulfuric acid, hydrochloric acid, perchloric acid and mixtures thereof may be added to the catalyst in step 2).

At the start of step 1) a small quantity of the intermediate compound obtained at the end of step 1) itself may be added, as the diols present in it encourage activation of the reaction. The said intermediate compound may be added in a quantity of ≤5%, preferably ≤3% by weight with respect to the starting oil.

Advantageously, during the course of step 1) of the process according to the invention air or inert gas (e.g. nitrogen) are caused to flow in order to remove part of the water produced in the process. Excessive dilution of $H_2O_2$ is avoided in this way. An alternative to the flow of these gases is evaporation under vacuum.

The reaction temperatures for step 1) and step 2) advantageously lie between 45 and 95° C., preferably between 50 and 90° C. In particular, the reaction temperature in step 1) is advantageously between 55 and 80° C., while the reaction temperature in step 2) is advantageously between 55 and 90° C., even more advantageously between 60 and 80° C. Advantageously, when carrying out both step 1) and step 2) of this process, the reaction time (that is the average residence time in the reactors in the case of a continuous process) is between 2 and 8 hours for each step.

In a preferred embodiment of the process the intermediate product resulting from step 1) containing vicinal diols is fed directly to the reactor in which step 2) is carried out, with the effect of an advantageous decrease in reaction time, thanks to the greater reactivity of the intermediate product itself, together with a significant increase in reaction yield.

Steps 1-2) of the process may advantageously be carried out at atmospheric pressure or, in any event, moderate oxygen partial pressures, with obvious advantages from the point of view of industrial production.

Step 1) is preferably carried out at atmospheric pressure or under slight vacuum.

Step 2) is preferably carried out with air at a pressure of ≤50 bar, preferably ≤30 bar.

According to one aspect of the invention these steps 1-2) are carried out in continuous reactors. The use of such continuous reactors makes it possible to reduce reaction volumes, aiding the exchange of heat. In a preferred embodiment one or more reactors of the CSTR (Continuous Stirred-Tank Reactor), possibly placed in series, are used.

Continuous reactors of the gas/liquid type are advantageously used in step 2). External recirculation (Loop CSTR) reactors, which encourage contact between the oxidising agent in the gaseous phase and the reaction mixture in the liquid phase, are preferably used when the oxidising agent is air.

Both steps 1) and 2) are preferably carried out without the addition of organic solvents. The intermediate product obtained from step 1) is fed to step 2), where it is caused to react with oxygen or a compound containing oxygen without the need for any purification treatment.

In a preferred embodiment of the process the catalyst is not removed at the end of step 1).

In a preferred embodiment of the process step 2) is carried out without the addition of water, apart from that in which the catalyst is dissolved. Advantageously said step 2) comprises an aqueous phase and an organic phase having a water/diol ratio by weight which is advantageously kept below 3:1, preferably below 1:1 and more preferably below 1:3 throughout the time of the oxidation reaction.

Advantageously, the aqueous phase is separated from the organic phase at the end of step 2). The aqueous phase can contain the catalysts for steps 1) and 2), and these in turn may be recovered and optionally recycled, possibly after suitable preliminary treatments, as catalysts for step 1) or step 2). One example of a preliminary treatment which makes it possible to reuse tungsten-based catalysts in step 1) is described in patent application WO 2016/116479. In an alternative embodiment of the process the aqueous phase separated at the end of oxidative cleavage step 2) containing the catalysts for steps 1) and 2) is fed back to the reactor for step 2), together with or as an alternative to fresh catalyst, after the addition of a suitable quantity of base, as described in International patent application PCT/EP2017/063613, incorporated here as a reference.

In a preferred embodiment of the process in which oil having a high oleic content is used as the starting material, the organic phase substantially comprises pelargonic acid and triglycerides of azelaic, palmitic, stearic and dihydroxystearic acids.

In step 3) of the process, the organic phase obtained as the oxidative cleavage product is fed to equipment suitable for separating the saturated monocarboxylic acids from the triglycerides containing saturated carboxylic acids having more than one carboxyl functional group. The separation is advantageously performed by means of distillation and/or evaporation processes. All distillation and/or evaporation processes which do not result in strong thermal stress on the mixture of products obtained in step 2), such as for example distillation in the flow of steam, molecular distillation, or evaporation in thin film or falling film evaporators are preferred. In a preferred embodiment of the process the monocarboxylic acids are separated from the triglycerides by evaporation using thin film evaporators.

In addition to the triglycerides of carboxylic acids having more than one acid functional group, the organic phase which is mixed with water in step a) of the process according to the invention also comprises partial esters of glycerine with at least a dicarboxylic acid.

By "partial esters of glycerine" are meant in this application monoglycerides and/or diglycerides, i.e. esters of glycerine with one or two carboxylic acids which may be the same or different. Thus, monoglycerides of carboxylic acids, diglycerides of carboxylic acids or their mixtures are selected, the said monoglycerides of carboxylic acids and the said mixtures of monoglycerides and diglycerides of carboxylic acids being preferred. Even more preferred are monoglycerides of carboxylic acids.

According to a preferred aspect of the invention the said partial esters of glycerine contain carboxylic acids selected from the monocarboxylic acids and the dicarboxylic acids present in the starting triglycerides for which examples have been given above, or mixtures thereof.

The said partial esters comprise at least one acyl group of a dicarboxylic acid and advantageously derive from the partial hydrolysis product of the triglycerides undergoing hydrolysis according to the invention.

The said partial esters of glycerine are preferably fed to step a), premixed together with dicarboxylic acids and/or glycerine, i.e. in the form of a mixture.

The said mixture advantageously has an acid number (understood to be the quantity of KOH, expressed in mg, used to neutralise the acidity of 1 g of substance) of more than 150 mg KOH/g, more preferably over 200 mg KOH/g. The acid number is determined in accordance with standard ASTM D974-07 in the presence of phenolphthalein.

The starting triglycerides of carboxylic acids having more than one acid function which undergo the process of the invention have typically an acid number of between 100-300 mg KOH/g. The organic phase of step a) after the addition of the mixture comprising partial esters of glycerine has an acid number of between 150-300 mg KOH/g. The addition of the mixture comprising partial esters of glycerine therefore does not significantly affect the acidity of the organic phase.

According to a preferred aspect of the process the said mixture comprises or preferably constitutes:
 i) from 20 to 80% of dicarboxylic acids, preferably from 40 to 70%;
 ii) from 0.5 to 30% of glycerine, preferably from 10 to 30%;
 iii) from 0.5 to 70% of partial esters of glycerine (mono- and/or diglycerides), preferably from 1 to 20%,
 iv) from 0 to 30% of monocarboxylic acids, preferably from 0 to 20%.

These percentages relate to the dry composition of the mixture and are intended to refer to the percentage area measured using GC analyses, carried out for example using a gas chromatograph equipped with a ZB-5Msi-Phenomenex capillary column (5% phenyl-95% dimethylpolysiloxane, 30 m×0.25 mm×0.25 µm), split mode injector (350° C.; split flow=30 ml/min; split ratio=25) and an FID detector (350° C.), with the following temperature gradient: 60° C. (4 min)-8° C./min-130° C. (2 min)-3° C./min-155° C.-15° C./min-325° C. (10 min); carrier: helium (1.2 ml/min).

According to one particularly advantageous aspect of the invention the said mixture comprising dicarboxylic acids, glycerine and partial esters of glycerine is obtained through the hydrolysis process of step b). For example some of the reaction product from step b) may be recycled to step a); this recycling is optionally preceded by a purification treatment. According to another aspect of the invention, the said mixture comprising dicarboxylic acids, glycerine and partial esters of glycerine is obtained from the hydrolysis product at the end of step c), i.e. after the dicarboxylic acids have been at least partially separated out, preferably through the treatment of purifying a portion of the hydrolysis product separated out in the aqueous phase.

The said purification treatments typically comprise one or more operations selected from crystallisation, solvent extraction or concentration.

In the case in which it is prepared from the product of the hydrolysis process, the mixture comprising dicarboxylic acids, glycerine and glycerine esters, which is mixed with the starting triglycerides of carboxylic acids having more than one acid functional group may contain water in variable quantities. The organic component of the said mixture in every case preferably corresponds to 3-20% by weight, more preferably 5-15% by weight, of the organic phase (comprising the said starting triglycerides) fed to the hydrolysis reactor.

The aforesaid mixture comprising partial esters of glycerine is fed to step a) of the process according to the invention, together or separately with respect to the starting triglycerides. According to a preferred aspect of the invention the said mixture comprising partial esters of glycerine is premixed with the starting triglycerides of carboxylic acids having more than one acid functional group, obtaining an organic phase which is subsequently mixed with water.

The mixing in step a) is advantageously preceded by heating of the components to temperatures of typically between 50 and 100° C.

The ratio by weight between water and organic phase (comprising the said starting triglycerides and the said mixture comprising partial esters of glycerine) preferably lies between 1:2 and 5:1, more preferably between 1:1 and 5:1. The said ratio is preferably held constant during the hydrolysis reaction in step b).

The hydrolysis reaction in step b) is carried out using water (or steam) at temperatures of between 150 and 350° C., typically between 180 and 320° C., and at pressures typically between 10 and 200 bar, with or without the addition of a catalyst.

According to a preferred aspect of the invention the process is carried out at temperatures between 240 and 320° C. and at pressures between 40 and 110 bar. According to a yet more preferred aspect the said process is carried out at temperatures of between 260 and 310° C. and at pressures between 67 and 110 bar, or maintaining a pressure of approximately 10-20 bar above the equilibrium vapor pressure. By adopting the above operating conditions, the process of the present invention allows to obtain yields of hydrolysis higher than those obtainable with the known processes in more severe conditions.

According to one aspect of the process in which the hydrolysis reaction is performed with water at 240-310° C. in one or more tubular reactors (Plug Flow Reactors), the ratio between water and organic phase is advantageously between 1:1 and 3:1.

The reaction time for the hydrolysis step is generally between 1 and 180 minutes and varies according to the type of reactor used; in the case of a tubular reactor, it is preferably between 1 and 60 minutes, more preferably between 3 and 30 minutes. Advantageously the hydrolysis reaction in a tubular plug flow reactor achieves a yield of more than 60% calculated on the basis of a gas chromatography analysis of the composition of the hydrolysis product compared with that of the total hydrolysis product deriving from saponification of the starting mixture, in less than 20 minutes.

In accordance with a preferred aspect, the reaction is carried out in a tubular reactor at temperatures of between 260 and 310° C., at a pressure of between 67 and 110 bar, and with a ratio between the quantity of water and organic phase during the reaction that is preferably 2:1 or higher and below 3:1.

The mixture obtained in step a) of the process is typically fed to the reactor of step b) hot, at a temperature preferably greater than 240° C.

In the hydrolysis reactor the said mixture is then further heated to reach temperatures of preferably between 270 and 305° C., in times of preferably less than 10 minutes and more preferably between 2 and 5 minutes.

The hydrolysis reaction is then advantageously performed holding the reagents at temperatures between 270 and 305° C. at a pressure of 75-95 bar for times of less than 30 minutes and preferably between 15 and 25 minutes.

According to a particularly advantageous aspect of the invention the organic phase mixed with water during step a) contains from 5 to 15% by weight of a mixture comprising (with respect to the sum of the areas of the peaks relating to compounds i-iv from the GC analysis):
  i) from 40 to 70% of dicarboxylic acids;
  ii) from 10 to 30% of glycerine;
  iii) from 1 to 20% of partial esters of glycerine (mono- and/or diglycerides),
  iv) from 0 to 20% of monocarboxylic acids,
while the hydrolysis reaction in step b) is carried out at a temperature below 285° C. at a pressure of preferably between 75 and 95 bar, for times of between 15 and 25 minutes. These conditions make it possible to achieve high efficiency in the hydrolysis reaction, similar to that obtained at temperatures of at least 300° C. in the absence of the aforesaid mixture.

Without wishing to be bound by theory, it is believed that the mixture comprising partial esters of glycerine with at least a dicarboxylic acid favors the contact between the organic phase and the water during the hydrolysis reaction even under milder conditions. A further advantage of the process according to this invention lies in the fact that the reaction can be effectively performed in the absence of catalysts or other added additives, such as for example, surfactants, which would require subsequent separation from the reaction product, and without subjecting the starting mixture to preliminary treatments.

The reaction may however be further assisted, for example by the addition of surfactants and/or catalysts, such as acid, organic or inorganic catalysts. Examples of inorganic acids suitable for addition to the reaction mixture are sulfuric, hydrochloric, perchloric, nitric, phosphoric or hydrofluoric acids; examples of organic acids are methane sulfonic, naphthalene sulfonic, toluene sulfonic acids, carboxylic acids preferably having a low molecular weight, such as formic, acetic or propionic acids, heterogeneous acids such as strongly acid ion exchange resins and supported transition metals, for example, catalysts supported on a zirconium base.

The product leaving the hydrolysis reactor contains water in variable quantities, depending upon the hydrolysis conditions used, together with glycerine, carboxylic acids with one or more acid functional groups and any partial esters of glycerine due to incomplete hydrolysis, which are distributed in the aqueous phase or in the organic phase, depending upon their relative solubilities.

In step c) of the process the product leaving the hydrolysis reactor undergoes one or more separation operations to remove the dicarboxylic acids released during the hydrolysis reaction.

According to one aspect of the process an aqueous phase comprising mainly glycerine, its esters and variable quantities of water-soluble carboxylic acids present in the hydrolysis product are separated from the remaining part of the hydrolysis product in the organic phase. This operation is carried out in accordance with procedures known to those skilled in the art, for example by decanting or centrifuging. In cases where the dicarboxylic acids present in the reaction product mainly comprise azelaic acid, the separation is preferably performed by decanting, raising the hydrolysis product to temperatures of between 60 and 90° C. at a pressure close to atmospheric (approximately 1 bar).

This separation in step c) preferably comprises one or more operations, selected for example from degassing, washing with water in addition to that fed in during the hydrolysis reaction and/or the addition of suitable quantities of inorganic solvents immiscible with water, which have the function of assisting separation of the two phases.

Examples of solvents suitable for assisting separation of the aqueous phase from the organic phase are hydrocarbons such as hexane, octane, nonane or mixtures thereof.

The addition of octane in quantities less than 10%, preferably less than 5% and over 2% with respect to the weight of hydrolysis product is particularly advantageous.

According to a preferred aspect, the aqueous phase is separated out following degassing and decanting.

The operation of separating the two phases may be carried out one or more times, possibly adding fresh water and carrying out one or more successive washes of the separated organic phase, for example, counter-currently.

The aqueous phase separated in this way can then undergo further separation and concentration treatments with a view to removing any impurities and recovering the glycerine and dicarboxylic acids present therein. These operations make it possible to obtain a mixture comprising dicarboxylic acid, glycerine and its esters, which can be recycled by feeding it again to the hydrolysis reaction in the process according to the invention.

The organic phase separated from the product leaving the hydrolysis reactor essentially contains saturated carboxylic acids with more than one acid functional group (dicarboxylic acids) and monocarboxylic acids, which may be substituted (hydroxy acids and keto acids), which may be released following the hydrolysis reaction, in addition to triglycerides and their oligomers deriving from incomplete hydrolysis of the initial mixture. They may also contain residues of water and organic solvent, which are advantageously removed before passing to subsequent stages in processing with a view to separating out and purifying the individual components, for example, by distillation and/or evaporation and/or crystallisation.

The invention will be illustrated below through a number of examples which are intended to be for illustrative purposes and not limiting the invention.

EXAMPLES

The starting material comprising triglycerides of carboxylic acids having more than one functional group was prepared according to the process for the oxidative cleavage of sunflower oil described in patent application WO 2008/138892. In particular, triglycerides containing azelaic acid obtained as a distillation residue at the end of step c) of separating out the monocarboxylic acids, performed as described in Example 1 of the aforesaid application, were used.

Analysis of the Hydrolysis Product

The quantitative composition of the hydrolysis product was determined by gas chromatography with reference to the calibration curve for each component with respect to an internal standard. Each sample was dissolved in a solution of chloroform containing the internal standard and then derivatised with BSTFA (N,O-Bis(trifluoroacetamide)) for at least 3 hours at 70° C. After this period of time 1 µl of the resulting solution was sampled and placed in the TRACE GC ULTRA-Thermo Scientific gas chromatograph, fitted with a ZB-5Msi-Phenomenex capillary column (5% phenyl-95% dimethylpolysiloxane, 30 m×0.25 mm×0.25 µm) and a FID detector, set up as described below:

heater: 60° C.-4 min
   8° C./min-130° C.-2 min
   3° C./min-155° C.
   15° C./min-325° C.-10 min
carrier: helium 1.2 ml/min;
injector: split mode
   T=350° C.;
   split flow=30 ml/min;
   split ratio=25;
detector: FID, T=350° C.

The yield from the hydrolysis reaction was compared with that from the total hydrolysis product deriving from saponification of the starting mixture using a 5 M NaOH solution, extracted in chloroform after acidification with HCl. The yields obtained were also confirmed by the final acidity value, determined by volumetric acid-base titration of the hydrolysis product and compared with that of the saponification product of the starting mixture.

Comparative Examples 1-2

1000 g of distillation residue (mainly comprising triglycerides of azelaic acid obtained as indicated above) were mixed with water in a ratio of 2:1 by weight, using a static mixer. The emulsion so obtained was subsequently heated to a temperature of 240° C. and fed via a high pressure pump to a hydrolysis reactor of the tubular type, characterised by a length of 74 metres and an internal diameter of 3 mm. The overall throughput of the water/oil mixture was approximately 3 kg/h.

The hydrolysis reactor operated at conditions of 280° C. and 80 bar (Comparative Example 1) and 300° C. and 95 bar (Comparative Example 2) for a reaction time of 17.5 minutes.

At the end of the reaction the reaction product from step b) underwent GC analysis. The reaction yield obtained in both cases is shown in Table 1.

The reaction product was cooled to a temperature of between 80 and 85° C., a quantity of octane equal to 4% by weight was added, and the product was decanted, separating an aqueous phase from the organic phase, mainly containing azelaic acid.

Examples 3-4

In a container fitted with a mechanical stirrer and thermostatted at a temperature of 80° C., 900 g of distillation residue (mainly comprising triglycerides of azelaic acid) were premixed with 100 g of a mixture having the following composition (GC areas %):
   65.1% of dicarboxylic acids (in which 13.9% was azelaic acid and 16.5% suberic acid),
   17.3% of glycerine
   17.6% of monoglycerides of dicarboxylic acids.

After 2000 g of water had been added the resulting mixture was fed to the hydrolysis reactor in the manner described in Comparative Examples 1-2, at 280° C. and 80 bar (Example 3) and 300° C. and 95 bar (Example 4) respectively, for a reaction time of 17.5 minutes. The hydrolysis yields are shown in the table below:

TABLE 1

| Example | Temperature (° C.) | Pressure (bar) | Yield from hydrolysis (% GC) |
| --- | --- | --- | --- |
| 1- comparative | 280 | 80 | 67.4 |
| 2- comparative | 300 | 95 | 83.0 |
| 3 | 280 | 80 | 84.6 |
| 4 | 300 | 95 | 84.7 |

It will be noted that, in the presence of a mixture comprising partial esters of glycerine according to the invention (Examples 3-4) the reaction yields are higher than those obtained in their absence (comparative Examples 1-2). Particularly, when operating at 280° C./80 bar (Example 3), an increase of more than 25% in the hydrolysis yield in comparison with that obtained under the same conditions in Comparative Example 1 is obtained. The yield achieved under these conditions also reaches the values obtained at 300° C./95 bar (Example 4), demonstrating the possibility that milder process conditions may be used.

Example 5

Example 3 was repeated, but performing the reaction at a temperature of 260° C. and a pressure of 90 bar. A hydrolysis yield of 79.5% was obtained in 17.5 minutes, i.e. considerably higher than the value of 67.4% obtained at 280° C. and 80 bar (Comparative Example 1).

Comparative Example 6

In a container fitted with a mechanical stirrer and thermostatted at a temperature of 80° C., 900 g of distillation residue (mainly comprising triglycerides of azelaic acid) were premixed with 100 g of a mixture having the following composition (GC areas %):
0.99% of pelargonic acid,
0.82% of glycerine
73.6% of monoglycerides of pelargonic acid
22.73% of diglyceride of pelargonic acid
1.86% of triglyceride of pelargonic acid.

After addition of the same amount of water and hydrolysis reaction as described in Example 3, a hydrolysis yield of 63.4% was obtained, showing that the addition of a mixture comprising partial glycerides of monocarboxylic acids affects negatively the hydrolysis yield.

Example 7

In a reactor fitted with a mechanical stirrer and thermostatted to a temperature of 80° C., 800 g of distillation residue was premixed with 200 g of product originating from the previous hydrolysis reaction, with a water content of 70% by weight. The organic component of this product had the following composition (GC areas %):
56.1% of dicarboxylic acids (in which 47.6% was azelaic acid and 2.7% suberic acid),
24.2% of glycerine
2.1% of monoglycerides of dicarboxylic acids,
17.6% of monocarboxylic acids.

Water (1580 g, for an overall water:organic phase ratio of 2:1) was added to the mixture so obtained. When the resulting mixture was fed to the hydrolysis reactor and the reaction was carried out at 280° C. and 80 bar, as in Example 3, a yield of 76.7% was obtained, i.e. higher than that obtained under the same conditions in the absence of the mixture comprising partial esters of glycerine according to the invention (Comparative Example 1).

The invention claimed is:

1. A process for the preparation of dicarboxylic acids from triglycerides of carboxylic acids having more than one acid functional group comprising the steps of:
    a) mixing water with an organic phase consisting of triglycerides of carboxylic acids having more than one acid function and from 3 to 20% by weight with respect to the weight of the organic phase of a mixture comprising partial esters of glycerine with at least a dicarboxylic acid; and
    b) hydrolysing the mixture obtained at the end of step a) in one or more hydrolysis reactors at temperatures of between 150 and 350° C., and at pressures corresponding to or higher than the equilibrium vapor pressure;
    c) separating the dicarboxylic acids from the hydrolysis product obtained in step b).

2. The process according to claim 1 in which the said organic phase of step a) comprises from 0.01 to 15% by weight, of partial esters of glycerine with respect to the weight of the organic phase.

3. The process according to claim 1 in which the mixture comprising partial esters of glycerine of step a) further comprises dicarboxylic acids and/or glycerine.

4. The process according to claim 2 in which the said mixture comprises with respect to the sum of the areas of the peaks of components i-iv from the GC analysis:
    i) from 20 to 80% of dicarboxylic acids;
    ii) from 0.5 to 30% of glycerine;
    iii) from 0.5 to 70% of partial esters of glycerine; and
    iv) from 0 to 30% of monocarboxylic acids.

5. The process according to claim 1, in which the said mixture comprising partial esters of glycerine is prepared from the hydrolysis product obtained in step b).

6. The process according to claim 5 in which the said mixture is further prepared by means of one or more operations selected from crystallisation, solvent extraction or concentration.

7. The process according to claim 1 in which the ratio by weight between the quantity of water and organic phase in step a) is between 1:2 and 5:1.

8. The process according to claim 1 in which step b) is carried out at temperatures between 240 and 320° C. and at pressures of between 40 and 110 bar.

9. The process according to claim 8 in which step b) is carried out at temperatures between 260 and 310° C. and at pressures of between 67 and 110 bar.

10. The process according to claim 8 in which the reaction time for step b) is between 1 and 60 minutes.

11. The process according to claim 1 in which the said reactors in step b) are plug flow tubular reactors.

12. The process according to claim 1 in which the said mixture constituting from 3 to 20% by weight of the organic phase in step a) comprises, with respect to the sum of the areas of the peaks relating to components i-iv, from the GC analysis:
    i) from 40 to 70% of dicarboxylic acids;
    ii) from 10 to 30% of glycerine;
    iii) from 1 to 20% of partial esters of glycerine (glycerides); and
    iv) from 0 to 20% of monocarboxylic acids,
    and in which step b) is carried out at a temperature below 285° C. and a pressure of between 75 and 95 bar, for times of between 15 and 25 minutes.

13. The process according to claim 1 in which the said organic phase in step a) is prepared by premixing triglycerides of carboxylic acids having more than one acid functional group and the said mixture comprising partial esters of glycerine.

14. The process according to claim 1 in which the said triglycerides of carboxylic acids having more than one acid functional group are prepared from triglycerides of unsaturated carboxylic acids present in vegetable oils or animal fats through oxidative cleavage reactions.

15. The process according to claim 14 in which the said triglycerides of unsaturated carboxylic acids are obtained by oxidative cleavage processes in which peroxides and $O_2$ or mixtures containing $O_2$ are used.

16. The process according to claim 1 carried out starting from vegetable oils comprising triglycerides of unsaturated acids and comprising, before step a), the steps of:
    1) reacting the said triglycerides of unsaturated carboxylic acids with an oxidising agent and a catalyst, activating the oxidisation reaction of the olefin double bond in order to obtain an intermediate compound containing vicinal diols, and
    2) reacting the said intermediate compound containing vicinal diols, an oxidising agent containing molecular oxygen and a catalyst activating the oxidation reaction of the vicinal diols to carboxyl groups, obtaining monocarboxylic acids and triglycerides having more than one acid functional group; and
    3) separating out a fraction of the said monocarboxylic acids, obtaining a mixture comprising the said triglycerides of carboxylic acids having more than one acid functional group.

17. The process according to claim 2 in which the mixture comprising partial esters of glycerine of step a) further comprises dicarboxylic acids and/or glycerine.

18. The process according to claim 2, in which the said mixture comprising partial esters of glycerine is prepared from the hydrolysis product obtained in step b).

19. The process according to claim 3, in which the said mixture comprising partial esters of glycerine is prepared from the hydrolysis product obtained in step b).

20. The process according to claim 4, in which the said mixture comprising partial esters of glycerine is prepared from the hydrolysis product obtained in step b).

\* \* \* \* \*